United States Patent
Nakajima et al.

(10) Patent No.: US 7,207,937 B2
(45) Date of Patent: Apr. 24, 2007

(54) OBJECTIVE LENS UNIT, IN-VIVO EXAMINATION APPARATUS AND ADAPTOR

(75) Inventors: Chika Nakajima, Chofu (JP); Yoshihisa Tanikawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/390,368

(22) Filed: Mar. 28, 2006

(65) Prior Publication Data

US 2006/0219934 A1   Oct. 5, 2006

(30) Foreign Application Priority Data

Mar. 30, 2005   (JP) ............................. 2005-098426

(51) Int. Cl.
- A61B 1/002 (2006.01)
- A61B 1/07 (2006.01)
- G02B 6/20 (2006.01)

(52) U.S. Cl. ............... 600/129; 600/138; 600/175; 600/176; 600/182; 396/529; 396/530; 359/425; 359/704

(58) Field of Classification Search ............... 600/129
See application file for complete search history.

(56) References Cited

U.S. PATENT DOCUMENTS

| | | | |
|---|---|---|---|
| 4,753,224 A | | 6/1988 | Tojo |
| 5,547,457 A | * | 8/1996 | Tsuyuki et al. ............ 600/175 |
| 5,554,100 A | * | 9/1996 | Leiner et al. ............... 600/182 |
| 5,603,687 A | * | 2/1997 | Hori et al. .................. 600/166 |
| 5,647,840 A | * | 7/1997 | D'Amelio et al. .......... 600/169 |
| 5,651,759 A | * | 7/1997 | Leiner et al. ............... 600/182 |
| 5,718,664 A | * | 2/1998 | Peck et al. .................. 600/178 |
| 5,812,887 A | * | 9/1998 | Nomura et al. ............... 396/72 |
| 6,152,872 A | * | 11/2000 | Peck et al. .................. 600/160 |
| 2005/0259933 A1 | * | 11/2005 | Temelkuran et al. ........ 385/123 |
| 2005/0259934 A1 | * | 11/2005 | Temelkuran et al. ........ 385/125 |
| 2005/0267330 A1 | * | 12/2005 | Deppmeier et al. ......... 600/114 |
| 2006/0219934 A1 | * | 10/2006 | Nakajima et al. .... 250/396 ML |

FOREIGN PATENT DOCUMENTS

| | | |
|---|---|---|
| EP | 0 690 327 A2 | 1/1996 |
| GB | 2 309 546 A | 7/1997 |
| JP | 07-222754 | 8/1995 |
| JP | 11-076155 | 3/1999 |
| JP | 11-313796 | 11/1999 |

\* cited by examiner

Primary Examiner—Nikita Wells
Assistant Examiner—Benard Souw
(74) Attorney, Agent, or Firm—Pillsbury Winthrop Shaw Pittman LLP

(57) ABSTRACT

When examining a living organism exhibiting dynamic behavior such as pulsing, the dynamic behavior is suppressed and clear images are acquired. The invention provides an objective lens unit including a lens barrel for supporting optical components, wherein an end surface of the lens barrel is disposed farther towards the distal side than an optical component at the extreme distal end, and channel-shaped indented portions extending in the diametrical direction are formed in the end surface of the lens barrel.

4 Claims, 4 Drawing Sheets

US 7,207,937 B2

OBJECTIVE LENS UNIT, IN-VIVO EXAMINATION APPARATUS AND ADAPTOR

BACKGROUND OF THE INVENTION

1. Field of the Invention

The present invention relates to an objective lens unit, an in-vivo examination apparatus, and an adaptor.

2. Description of Related Art

Recently, in biological research, ion concentration, membrane potential, and so forth are visualized using fluorescence probes and optical microscopes. For example, so-called in-vivo examination (examination of internal organs and so on while the specimen is still living) is carried out using an individual laboratory animal as the specimen. With in-vivo examination, the examination site may easily shift or may become defocused because the object under examination exhibits motion such as pulsing, respiration, and so on.

One known method to eliminate such shifting of the examination site and defocusing is to use an apparatus that moves the entire microscope, including an imaging device, to track the motion of the object under examination (for example, see Japanese Unexamined Patent Application Publication No. HEI-7-222754).

However, with the apparatus disclosed in Japanese Unexamined Patent Application Publication No. HEI-7-222754, since it is necessary to drive the entire microscope, which is heavy, there is a problem in that it is not possible to move it at high speed. When examining the heart, for example, the pulse rate of a rat is about 350 beats/second and that of a mouse is about 620 beats/second. Therefore, it is extremely difficult to make the apparatus disclosed in the above-cited document track such high pulse rates.

BRIEF SUMMARY OF THE INVENTION

The present invention has been conceived in light of the circumstances described above, and it is an object thereof to provide an objective lens unit, an in-vivo examination apparatus, and an adaptor which enable clear images to be acquired from a living organism exhibiting dynamic behavior, particularly a living organism that moves with a short period.

In order to realize the object described above, the present invention provides the following solutions.

According to a first aspect, the present invention provides an objective lens unit including a lens barrel for supporting optical components. An end surface of the lens barrel is disposed farther towards the distal side than an optical component at the extreme distal end of the lens barrel, and channel-shaped indented portions extending in a diametrical direction are formed in the end surface of the lens barrel.

When the objective lens unit according to this aspect is attached to an examination apparatus, such as a microscope or the like, and in-vivo examination of a specimen such as a living organism is carried out, the specimen is restrained from moving in the optical axis direction by bringing the end surface of the lens barrel of the objective lens unit into close contact with the specimen. Therefore, even if the specimen exhibits dynamic behavior with a short period, by applying pressure thereto, it is possible to acquire clear, blur-free images.

According to this aspect, because the channel-shaped indented portions are formed in the end surface of the lens barrel, when there is a blood vessel in the specimen it is possible to seat the blood vessel inside the indented portions and to press the area other than the blood vessel with the end surface of the lens barrel. Therefore, it is possible to prevent the blood vessel from being squeezed during examination, and examination of the living organism can thus be carried out while maintaining normal conditions.

According to a second aspect, the present invention provides an in-vivo examination apparatus comprising the objective-lens unit described above.

According to this aspect, when there is a blood vessel in the specimen, the blood vessel can be seated inside the indented portions formed in the end surface of the lens barrel of the objective lens unit, and it is thus possible to carry out examination while pressing the region other than the blood vessel with the end surface of the lens barrel. Therefore, it is possible to prevent the blood vessel from being squeezed during examination, and it is thus possible to carry out examination of the living organism while maintaining normal conditions.

According to a third aspect, the present invention provides a tube-shaped adaptor for attaching to an end of a lens barrel supporting optical components in an objective lens unit, including a pressing surface disposed farther towards a distal side than an end surface of the lens barrel. Channel-shaped indented portions extending in a diametrical direction are formed in the pressing surface.

By attaching the adaptor according to this aspect of the invention to the end of the lens barrel of the objective lens unit, when the living organism is pressed with the pressing surface of the adaptor, a blood vessel is seated inside the indented portions formed in the pressing surface, and it is thus possible to suppress dynamic behavior of the living organism without squeezing the blood vessel. Therefore, even if the specimen exhibits dynamic behavior with a short period, by applying pressure thereto, it is possible to acquire clear, blur-free images.

In the aspect of the invention described above, it is preferably that the adaptor be removably attached to the end of the lens barrel.

When carrying out normal examination with the adaptor removed, and when carrying out examination of a blood vessel in a living organism or in-vivo examination of a living organism having a blood vessel, the adaptor is attached to the end of the lens barrel, and it is possible to suppress the dynamic behavior of the living organism without squeezing the blood vessel.

According to the present invention, when carrying out examination of a living organism that exhibits dynamic behavior, it is possible to suppress the dynamic behavior of the living organism without squeezing the blood vessel. Therefore, an advantage is afforded in that it is possible to acquire clear, blur-free images while preserving the viability of the specimen or while maintaining normal conditions, that is, without squeezing the living organism.

DETAILED DESCRIPTION OF THE INVENTION

An objective lens unit 1 and an in-vivo examination apparatus 2 according to an embodiment of the present invention will be described below with reference to the drawings.

Figure 1:
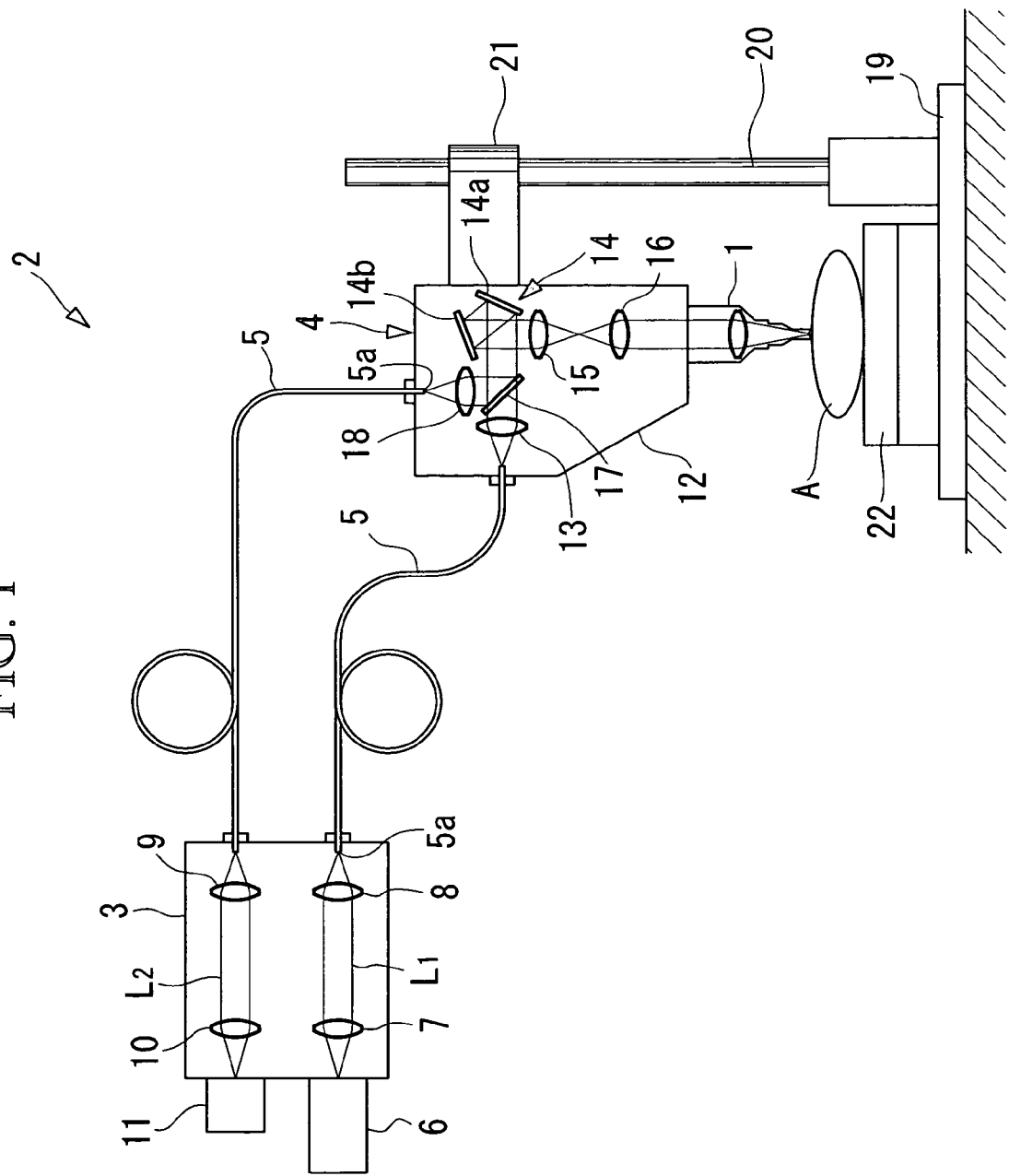
FIG. 1 is a schematic diagram showing, in outline, the overall configuration of an in-vivo examination apparatus according to an embodiment of the present invention.

As shown in FIG. 1, the in-vivo examination apparatus 1 according to the present invention includes an optical unit 3, an examination head 4, and first and second optical fibers 5 connecting the optical unit 3 and the examination head 4.

The optical unit 3 includes an excitation light source 6 for emitting excitation light L1 such as laser light, a collimator lens 7 for converting the emitted excitation light L1 into a collimated beam, a coupling lens 8 for focusing the collimated excitation light L1 onto an end 5a of the first optical fiber 5, a collimator lens 9 and focusing lens 10 for focusing fluorescence L2 returning via the second optical fiber 5, and a light detector 11 for detecting the focused fluorescence L2. The light detector 11 is, for example, a photomultiplier tube (PMT).

The examination head 4 includes a collimator lens 13 for converting the excitation light L1 from the excitation light source 6 into a substantially collimated beam, an optical scanning unit 14 for two-dimensionally scanning the collimated beam emitted from the collimator lens 13, a pupil-projection lens 15 for focusing the scanned excitation light L1 to form an intermediate image, and an imaging lens 16 for collecting the excitation light L1 forming the intermediate image and converting it into a collimated beam. All of these components are contained inside a housing 12. Also, the objective lens unit 1, which focuses the excitation light L1 from the imaging lens 16 and re-images it at a predetermined focal position, is attached to the housing 12.

Also provided inside the housing 12 are a dichroic mirror 17 and a coupling lens 18. The dichroic mirror 17 splits off from the excitation light L1 the fluorescence L2 produced in a specimen A and returning via the objective lens unit 1, the imaging lens 16, the pupil-projection lens 15, and the optical scanning unit 14. The coupling lens 18 focuses the split-off fluorescence L2 onto an end 5a of the second optical fiber 5.

The optical scanning unit 14 is a so-called proximity galvanometer mirror formed of two opposing galvanometer mirrors 14a and 14b, which can rock back and forth about two mutually orthogonal axes.

The examination head 4 includes a raising and lowering slider 21, which is raised and lowered by a driving device (not shown). The raising and lowering slider 21 is provided on a support stand 20 which rises vertically from a base 19. Reference numeral 22 in the figure is a stage for mounting the specimen A and supporting it in such a manner that it can move in the horizontal directions.

Figure 2:
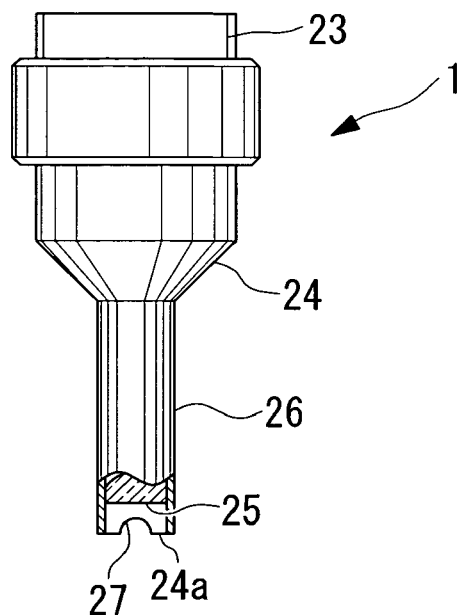
FIG. 2 is a partially cutaway front elevational view showing an objective lens unit provided in the in-vivo examination apparatus in FIG. 1.
Figure 3:
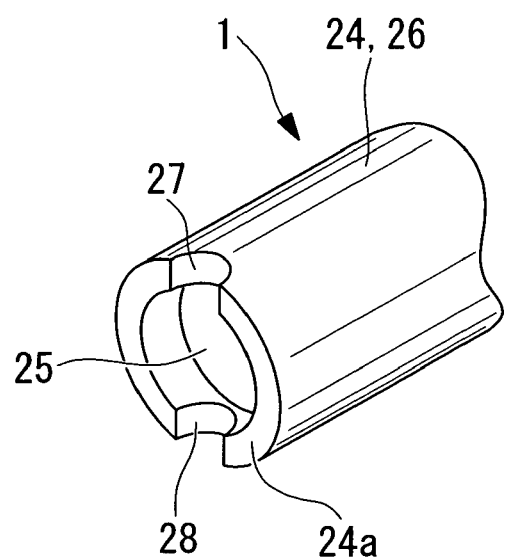
FIG. 3 is a perspective view showing an end surface of a lens barrel in the objective lens unit in FIG. 2.

As shown in FIG. 2, the objective lens unit 1 is configured to contain a plurality of optical components 25 inside a lens barrel 24, which is provided with a mounting thread 23 to enable attachment to and removal from the housing 12. The objective lens unit 1 according to this embodiment includes, at the end of the lens barrel 24, a cylindrical portion 26 with a diameter small enough to enable an end surface 24a thereof to be inserted inside the specimen A with minimal invasiveness. Indented portions 27 are provided in the end surface 24a of the lens barrel 24, as shown in FIGS. 2 and 3.

The end surface 24a of the lens barrel 24 is disposed farther in the distal direction than the optical component 25 disposed at the extreme distal end from among the plurality of optical components 25 supported in the lens barrel 24, for example, a cover glass. The indented portions 27 are formed in the shape of channels extending in the diametrical direction so as to form notches in the end surface 24a of the lens barrel 24, which are positioned on either side of the optical component 25.

The operation of the objective lens unit 1 and the in-vivo examination apparatus 2 according to this embodiment, having the above-described configuration, will be described below.

The excitation light L1 emitted from the excitation light source 6 in the optical unit 3 passes through the collimator lens 7 and the coupling lens 8, is focused onto the end 5a of the first optical fiber 5, and propagates through the first optical fiber 5 and into the examination head 4. After propagating through the first optical fiber 5, the excitation light L1 is substantially collimated by the collimator lens 13 and, in this state, is transmitted through the dichroic mirror 17 and is two-dimensionally scanned by the optical scanning unit 14.

The excitation light L1 scanned by the optical scanning unit 14 is then relayed via the pupil-projection lens 15, the imaging lens 16, and the objective lens unit 1, is emitted from the end of the objective lens unit 1, and irradiates the specimen A.

Then, by bringing the end surface 24a of the lens barrel 24 in the objective lens unit 1 into close contact with the specimen A and applying a predetermined pressure to the specimen A, it is possible to suppress the dynamic behavior of the specimen A, such as pulsing.

Therefore, when performing in-vivo examination of the living specimen A, such as a small laboratory animal, by irradiating the excitation light L1 onto the specimen A, while pressing the specimen A with the end surface 24a of the lens barrel 24, and detecting the fluorescence L2 emitted from the specimen A, it is possible to suppress motion of the examination site due to pulsation or the like of the living specimen A, which allows clear, blur-free images to be acquired.

In this case, with the objective lens unit 1 and the in-vivo examination apparatus 2 according to this embodiment, because the indented portions 27 are provided in the end surface 24a of the lens barrel 24, it is possible to prevent the examination site being squeezed around the entire circumference thereof, even though the ring-shaped end surface 24a is pressed against the specimen A.

Figure 4:
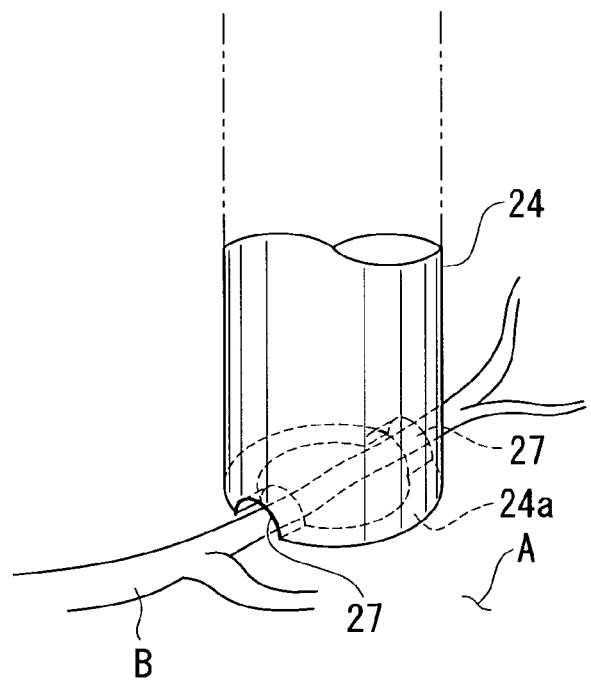
FIG. 4 is a perspective view showing the end surface of the barrel in the objective lens unit in FIG. 2 pressed against a living organism.

In other words, as shown in FIG. 4, if the object to be examined in the living specimen A is a blood vessel B, or if there is a blood vessel B in the vicinity of the examination site, the end surface 24a of the lens barrel 24 is pressed against the specimen A while allowing the blood vessel B to enter the field of view of the objective lens unit 1. Therefore, the blood vessel B is located so as to intersect the end surface 24a of the lens barrel 24 in the diametrical direction.

In such a case, by adjusting the angle of the objective lens unit 1 about the optical axis so that the blood vessel B is aligned with the indented portions 27 at the two locations formed in the end surface 24a of the lens barrel 24, it is possible to avoid squeezing the blood vessel B by seating it inside the indented portions 27, even though the specimen A is pressed by the end surface 24a of the lens barrel 24. As a result, even though the specimen A is pressed to suppress the dynamic behavior such as pulsing, it is possible to prevent normal blood flow from being impeded, and it is thus possible to perform in-vivo examination of the living specimen A under normal conditions.

The objective lens unit 1 and the in-vivo examination apparatus 2 according to this embodiment have been described in terms of an example in which the indented portions 27 are provided at two locations in a straight line in the diametrical direction of the end surface 24a of the lens barrel 24 in the objective lens unit 1. Instead of this, however, the indented portions 27 may be provided at three or more locations.

Figure 5:
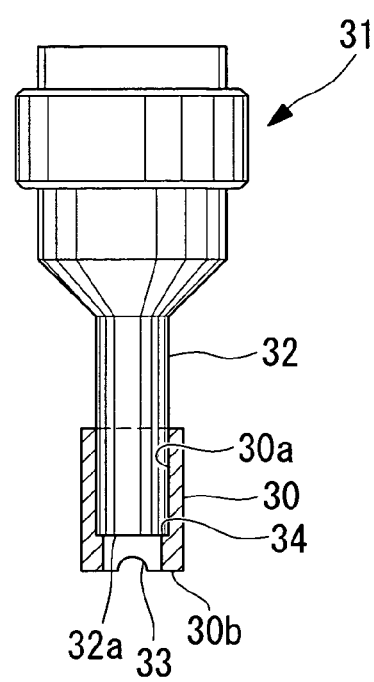
FIG. 5 is a longitudinal sectional view showing an adaptor according to an embodiment of the present invention attached to the tip of the objective lens unit.
Figure 6:
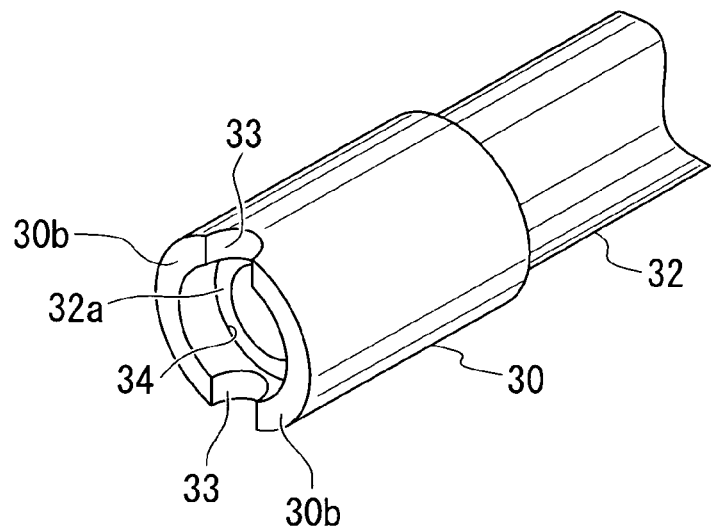
FIG. 6 is a perspective view showing the end surface of the adaptor in FIG. 5.

Next, an adaptor 30 according to an embodiment of the present invention will be described below with reference to FIGS. 5 and 6.

The adaptor 30 according to this embodiment is a tubular member that can be removably attached to the end of a lens barrel 32 in an objective lens unit 31. The adaptor 30 includes a coupling hole 30a for fitting to the end of the lens barrel 32 and two indented portions 33, extending in the diametrical direction, formed in an end surface 30b which is located at the tip when the adaptor 30 is attached to the tip of the end of the barrel 32.

A step portion 34 is provided inside the coupling hole 30a in the adaptor 30. An end surface 32a of the lens barrel 32 abuts against this step portion 34 when the adaptor 30 is fitted to the lens barrel 32. Therefore, by fitting the end of the lens barrel 32 into the coupling hole 30a in the adaptor 30 so that the end surface 32a thereof abuts against the step portion 34, it is possible to attach the adaptor 30 at a fixed position on the end of the lens barrel 32.

With the adaptor 30 according to this embodiment, having the configuration described above, by attaching it at a fixed position on the end of the lens barrel 32 and pressing the specimen A with the end surface 30b of the adaptor 30, it is possible to suppress dynamic behavior of the specimen A, such as pulsing.

Therefore, when performing in-vivo examination of a living specimen such as a small laboratory animal, by irradiating the specimen A with excitation light L1 and detecting the fluorescence L2 emitted from the specimen A while the specimen A is being pressed by the end surface 30b of the adaptor 30, it is possible to suppress motion of the examination site due to pulsing or the like of the living specimen A. Therefore, it is possible to acquire clear, blur-free images.

In this case, with the adaptor 30 according to this embodiment, because the indented portions 33 are provided in the ring-shaped end surface 30b which is pressed against the living specimen A, it is possible to prevent the examination site from being squeezed around the entire circumference thereof. In other words, by seating the blood vessel B inside the indented portions 33 formed in the end surface 30b of the adaptor 30, it is possible to prevent the blood vessel B from being squeezed. As a result, it is possible to prevent normal blood flow in the living specimen A from being impeded while allowing dynamic behavior of the specimen A, such as pulsing, to be suppressed.

According to this embodiment, removing the adaptor 30 from the end of the lens barrel 32 in the objective lens unit 31 allows normal observation to be carried out without using the adaptor 30. Also, by replacing the adaptor 30 with another one having a different distance between the end surface 30b and the step portion 34, it is possible to adjust the focal position of the objective lens unit 31.

Although the adaptor 30 according to this embodiment is removably attached to the end of the lens barrel 32 in the objective lens unit 31, it may instead be attached to the housing 12.

Figure 7:
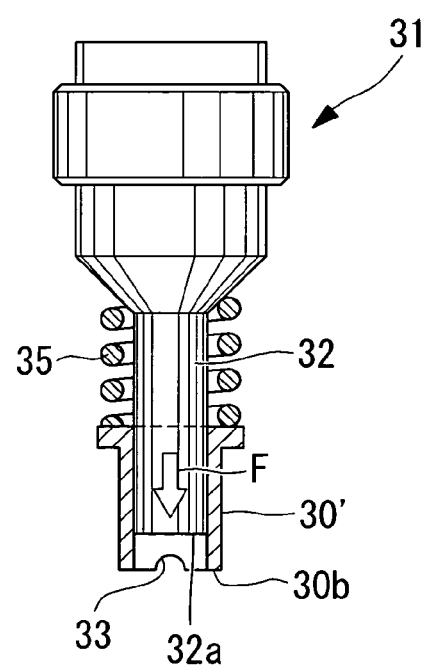
FIG. 7 is a longitudinal sectional view showing a modification of the adaptor in FIG. 5.

Furthermore, as shown in FIG. 7, an adaptor 30' may be attached to the lens barrel 32 of the objective lens unit 1 so as to be freely movable in the longitudinal direction thereof. A pressing force F which presses down the adaptor 30' may be applied by means of a coil spring 35 disposed between the lens barrel 32 and the adaptor 30' or by means of a weight (not shown in the drawing).

What is claimed is:

1. An objective lens unit comprising:
   a lens barrel for supporting optical components,
   wherein an end surface of the lens barrel is disposed farther towards the distal side than an optical component at the extreme distal end, and
   channel-shaped indented portions extending in a diametrical direction are formed in the end surface of the lens barrel.

2. An in-vivo examination apparatus comprising the objective-lens unit according to claim 1.

3. A tube-shaped adaptor for attaching to an end of a lens barrel supporting optical components in an objective lens unit, comprising:
   a pressing surface disposed farther towards a distal side than an end surface of the lens barrel,
   wherein channel-shaped indented portions extending in a diametrical direction are formed in the pressing surface.

4. An adaptor according to claim 3, wherein the adaptor is removably attached to the end of the lens barrel.

* * * * *